United States Patent [19]

Kobayashi et al.

[11] Patent Number: 4,698,550
[45] Date of Patent: Oct. 6, 1987

[54] HOLLOW CATHODE LAMP

[75] Inventors: Masayasu Kobayashi, Hamamatsu, Japan; Julius R. Eno, Jr., Basking Ridge, N.J.

[73] Assignee: Hamamatsu Photonics Kabushiki Kaisha, Hamamatsu, Japan

[21] Appl. No.: 731,328

[22] Filed: May 6, 1985

[51] Int. Cl.⁴ .............................................. H01J 17/06
[52] U.S. Cl. ..................................... 313/618; 313/632
[58] Field of Search ............... 313/618, 621, 631, 632, 313/613, 616

[56] References Cited

U.S. PATENT DOCUMENTS

| | | | |
|---|---|---|---|
| 3,233,136 | 2/1966 | Okagaki et al. | 313/618 X |
| 3,401,292 | 9/1968 | Cirri | 313/618 X |
| 3,869,643 | 3/1975 | Okagaki | 313/618 X |
| 4,320,321 | 3/1982 | Alexandrov | 313/618 |

FOREIGN PATENT DOCUMENTS 79660 10/1983 Japan .

OTHER PUBLICATIONS

"The Hollow Cathode Discharge as a Spectrochemical Emission Source," *Applied Spectroscopy Reviews*, 10(2), 201–255 (1975).

Primary Examiner—Palmer C. DeMeo
Assistant Examiner—Sandra L. O'Shea
Attorney, Agent, or Firm—Spencer & Frank

[57] ABSTRACT

The hollow cathode lamp can be used as a light source for the atomic absorption and scintillation spectroscopies. It contains a diffusion-protection cylinder to trap the cathode material by blocking the light emission window from the cathode material; the cylinder encloses the optical path leading from the cathode to the light emission window in a space between the cathode and the light emission window.

7 Claims, 10 Drawing Figures

FIG. I(A)
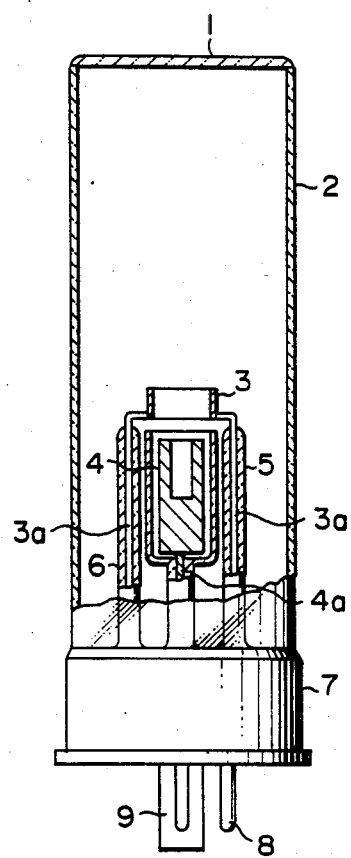
FIG. I(B)
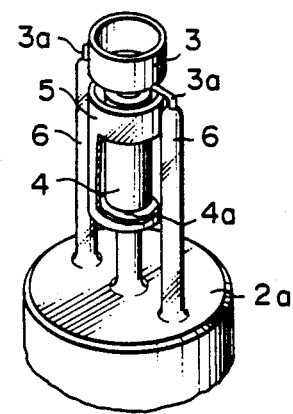

FIG. 2(A)
FIG. 2(B)
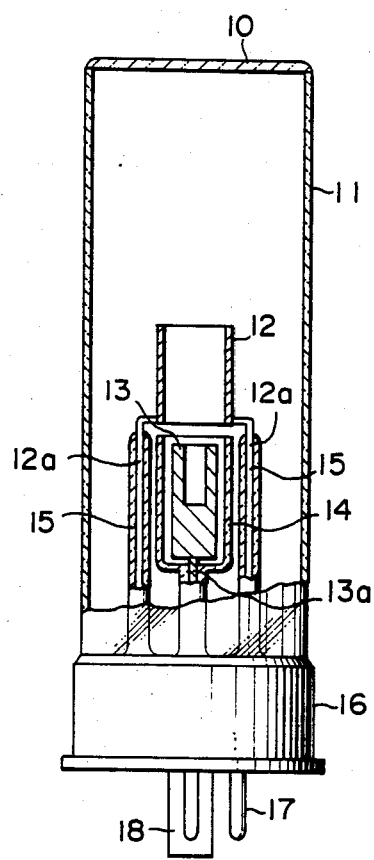
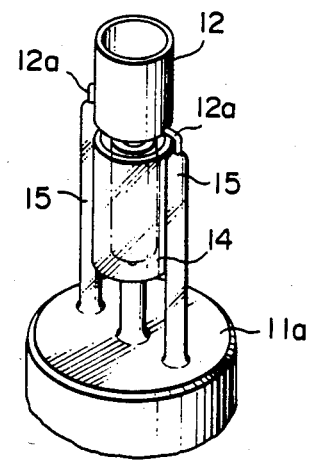

HOLLOW CATHODE LAMP

BACKGROUND OF THE INVENTION

The present invention relates to a hollow cathode lamp used as the light source for the atomic absorption and scintillation spectroscopies.

The structure of the conventionally fabricated hollow cathode lamp will be described referring to FIGS. 1(A) and 1(B).

FIG. 1(A) shows a cross-sectional view of the internal structure of the conventional hollow cathode lamp and FIG. 1(B) shows a perspective view of the electrode structure thereof.

Bulb 2 is fastened to base 7 to form a sealed envelope. A rare gas at a pressure of the order of torrs is filled in an envelope together with the electrodes which will be described hereafter.

Light generated inside bulb 2 is radiated outside through light emission window 1 at the top of bulb 2.

Cylindrical anode 3, with the same diameter as the cathode, is connected to the external circuit through anode leads 3a—3a which are connected to anode lead pin 9 fastened to base 7, and it is supported by base 7 within a space defined by bulb 2. Most of the surface of the anode leads 3a—3a are covered with an insulator covering 6 fastened to stem 2a of a bulb 2.

Hollow cathode 4, which constitutes a cylinder with a hollow at the center thereof, is connected to cathode lead pin 8 fastened to base 7 through cathode lead 4a.

Cathode lead 4a is covered with an insulator cover forming part of stem 2a of bulb 2. Extending upwardly from the end of this insulator cover is an insulator cylinder 5 which covers the cathode 4.

When a firing voltage of 400 to 600 volts DC is fed from the external circuit to the lamp, ionized gas molecules within an envelope collide with the inner wall of the cylindrical cathode 4 so as to evaporate the cathode material. The bright line spectrum of the material forming the cathode 4 can thus be obtained.

The cathode material evaporated from cathode 4 drifts into light emission window 1 by thermal diffusion and is deposited onto light emission window 1. This reduces the transmittivity of light emission window 1. If the hollow cathode lamp is operated at high current, a substantial quantity of cathode material is evaporated from the cathode 4 and the light emission window 1 is covered with the cathode material in a short period of time.

A disk with an aperture at the center thereof, if arranged in a space between cathode 4 and light emission window 1, blocks the light emission window 1 from the cathode material and protects it against decreasing of the transmittivity. (The structure of the disk with an aperture will be described referring to preferred embodiments of the present invention.) It has been found that the structure of the disk in the conventional hollow cathode lamp is not so advantageous as expected.

The objective of the present invention is to present an improved type of hollow cathode lamp constructed to keep the light intensity unchanged by blocking the light emission window from the cathode material which reduces the transmittivity when it adheres to the light emission window.

SUMMARY OF THE INVENTION

The hollow cathode lamp in accordance with the present invention, which can be used as a light source for the atomic absorption and scintillation spectroscopies, contains a diffusion-protection cylinder to trap the cathode material by blocking the light emission window from the cathode material, with this cylinder enclosing the optical path leading from the cathode to the light emission window in a space between the cathode and the light emission window.

BRIEF DESCRIPTION OF THE DRAWINGS

FIGS. 1(A) and 1(B) show the structure of the conventional hollow cathode lamp, FIG. 1(A) being a cross-sectional view of the internal structure thereof and FIG. 1(B) being a perspective view of the electrode structure thereof.

FIG. 2(A) shows a cross-sectional view of the first preferred embodiment of the hollow cathode lamp in accordance with the present invention, and FIG. 2(B) shows a perspective view of main electrodes for the preferred embodiment shown in FIG. 2(A).

PREFERRED EMBODIMENTS

Figure 3A:
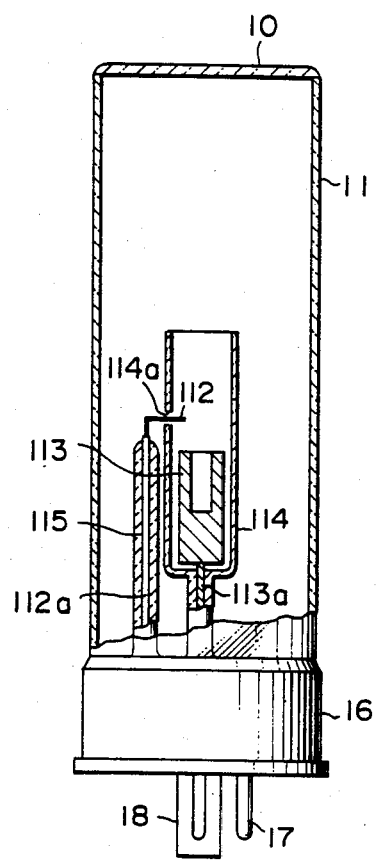
FIG. 3(A) shows a cross-sectional view of the second preferred embodiment of the hollow cathode lamp in accordance with the present invention.

The first embodiment of the hollow cathode lamp of this invention will be described referring to FIGS. 2(A) and 2(B).

Light emission window 10 is provided at the top of bulb 11. Cylindrical anode 12 made of stainless steel also acts as a diffusion protection cylinder to effectively trap the evaporated cathode material as well as performing the anode function.

Cylindrical anode 12 is supported by anode leads 12a—12a connected to anode lead pin 18 of base 16, and is covered with anode insulator material 15 together with the stem 11a.

Cathode 13 is a cylinder with a hollow at the center thereof and is connected to lead pin 17 of base 16 through lead 13a. Lead 13a is covered with an insulator material forming stem 11a.

A cathode enclosure 14 forming a cylinder to enclose the cathode 13 with insulator material is provided.

Figure 3B:
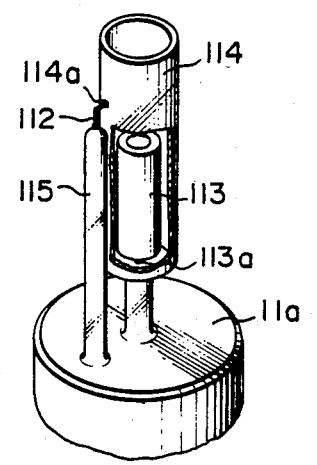
FIG. 3(B) shows a perspective view of main electrodes for the second embodiment shown in FIG. 3(A).

The second embodiment of the hollow cathode lamp according to this invention will be described referring to FIGS. 3(A) and 3(B).

The diffusion protection cylinder to trap the evaporated cathode material is formed by extending the cathode enclosure 114 consisting of an insulator cylinder toward the light emission window 10.

Anode 112 is of rod type and extends in front of cathode 113 via aperture 114a of within the diffusion protection insulator cylinder 114 covering the cathode 113. Anode pin 112a is covered with insulator 115 forming part of stem 11a.

The hollow cathode lamp with a disk-like shield in accordance with the conventional technique will be described referring to FIG. 4.

Light emission window 419 is provided at the top of bulb 420 wherein disk-like shield 421 acting as an anode and cylindrical cathode 422 are arranged.

Cylindrical cathode 422 is connected to lead pin 426 of base 425 through cathode lead 422a. The cathode 422 is enclosed by a cylinder 423 of insulating material, with this insulating material also covering the lead 422a.

The disk-like anode 421 is connected to lead pin 427 of base 425 through anode lead 421a.

Anode leads 421a-421a are covered with insulator material 424 forming a stem (not shown).

Figure 4:
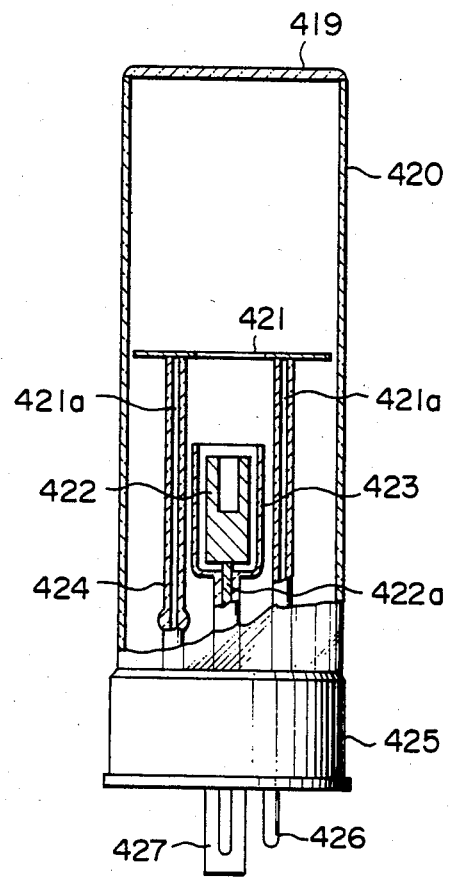
FIG. 4 shows a cross-sectional view of the hollow cathode lamp with a disk-like shield, in the conventional technique.
Figure 5:
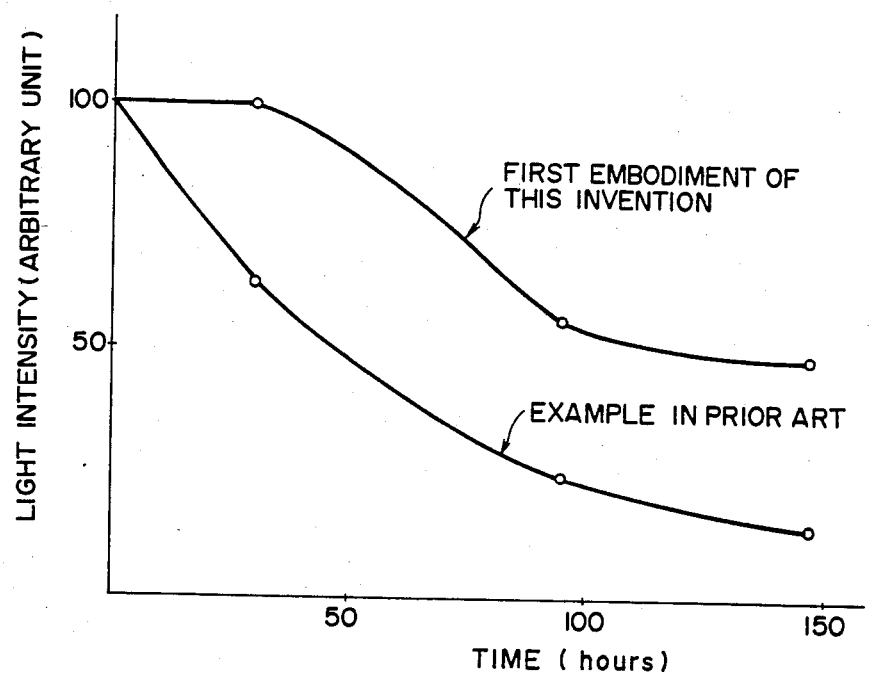
FIG. 5 shows a graph of the light intensity changes with elapsing of time for the first embodiment of the hollow cathode lamp compared with the example of the conventional hollow cathode lamp.

Now, let us compare the performance of the first embodiment (shown in FIG. 2) with that of the lamp of FIG. 4, referring to FIG. 5.

The performance of the hollow cathode lamp will be described referring to such a graph that the light intensity changes with elapsing of time for the first embodiment of the hollow cathode lamp when compared with those for an example of the conventional hollow cathode lamp. In FIG. 5, the light intensity at 324.7 nm radiated from Cu for zero operating time is assumed to be 100.

The cylindrical shield 12 of the first embodiment of the hollow cathode lamp (FIG. 2a) has an inner diameter of 13 mm and a length of 16 mm. The disk-like shield 421 of the conventional hollow cathode lamp (FIG. 4) has an inner diameter of 13 mm and an outer diameter of 34 mm, and it is arranged 16 mm apart from the front surface of the cathode 422.

The dimensions are specified so that light from the cathode can effectively be output through the entire area of the light emission window.

In both the first embodiment of this invention and the conventional version, the cathode was made of copper and the sealed gas was Ne at a pressure of eight torrs. These lamps were operated at a peak current of 260 mA clocked at a repetition rate of 50 pps with a duty factor of 1 to 11. Operation was continuous for 147 hours.

The intensity of the bright line spectrum for Cu at 324.7 nm was then measured. The hollow cathode lamp in accordance with the present invention, as shown in FIG. 5, had the light intensity which was equal to 50% of the initial value after being continuously operated for 147 hours. On the other hand, the conventional hollow cathode lamp of FIG. 4 had the light intensity which was equal to 50% of the initial value after continuously operated for 50 hours. and that which was equal to 15% of the initial value after being continuously operated for 147 hours.

After continuously being operated for predetermined periods of time, each of the hollow cathode lamps was destroyed. Thereafter, the light emission windows were taken out and their transmittivities were measured.

Assuming that the transmittivities before operation are 100%, the measured transmittivity of the light emission window for the hollow cathode lamp in accordance with the present invention was 48%, and that for the conventional hollow cathode lamp was 28%. The transmittivity for the hollow cathode lamp in accordance with the present invention cannot easily be stained by cathode material when compared with that for the conventional hollow cathode lamp.

The above phenomena can be understood as follows: The evaporated cathode material diffuses along a jigzag path while colliding with the sealed gas molecules due to thermal motion.

Much evaporated cathode material adheres to the cylindrical shield arranged along the path of diffusion motion when compared with that which adheres to the disk-like shield. The evaporated cathode material can easily be trapped by the shield in accordance with the present invention and a lesser quantity of the evaporated cathode material can be transported to the light emission window.

Next, the structure of th cylindrical shield will be described referring to a graph of FIG. 6 in which the light intensity changes with elapsing time for the first embodiment of the hollow cathode lamp are given under such conditions that the inner diameter of the cylindrical shield is kept unchanged and that the length thereof is changed.

The inner diameter of the cylindrical shield in the first embodiment of the hollow cathode lamp in accordance with the present invention was specified as 13 mm, and the length thereof was specified as 5 mm, 13 mm and 16 mm. The cathode material was made of copper and the sealed gas was Ne at eight torrs. An experiment was carried out by using three lamps.

Figure 6:
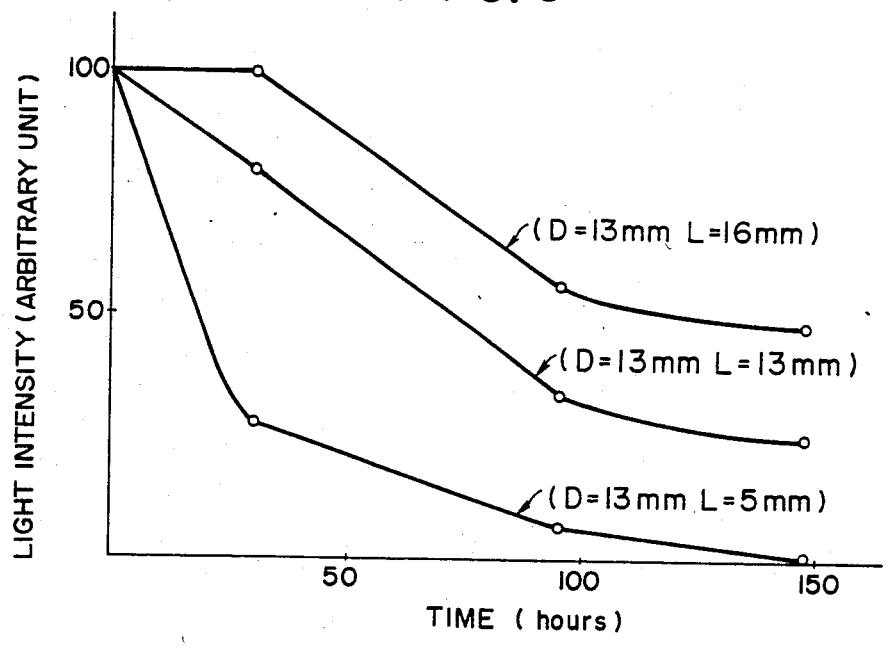
FIG. 6 shows such a graph that the light intensity changes with elasping of time for the first embodiment of the hollow cathode lamp are given under such conditions that the inner diameter of the cylindrical shield is kept unchanged and that the length thereof is changed.

Each hollow cathode lamp was continuously operated by a pulse signal with a duty factor of 1 to 11 as shown in FIG. 6 at a peak current of 260 mA at a repetition rate of 500 pps for a time of 147 hours.

The result of the experiment indicates that the length of the cylindrical shield should be at least 13 mm or more.

Another experiment was carried out under such condititons that the inner diameter of the cylindrical shield was specified as 8 mm, 13 mm and 16 mm, and that the length thereof was specified as 16 mm. The cathode material was made of copper and the shielded gas was Ne at eight torrs. Three lamps were used for the experiment.

Figure 7:
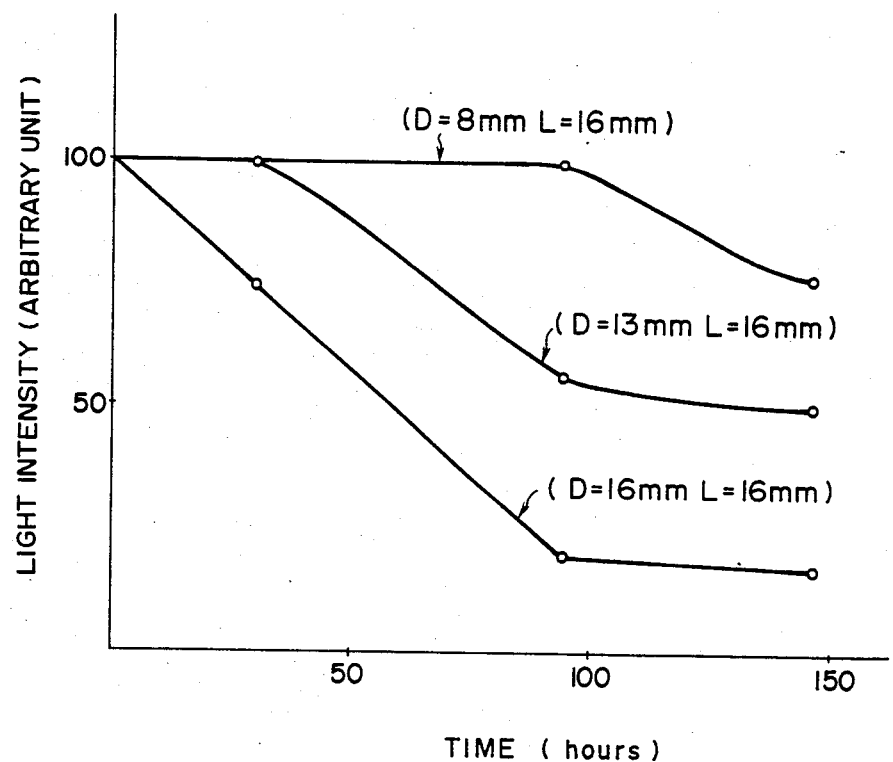
FIG. 7 shows a graph that the light intensity changes with elapsing of time for the first embodiment of the hollow cathode lamp are given under such conditions that the inner diameter of the disk-like shield is changed and that the length thereof is kept unchanged.

Each hollow cathode lamp was continuously operated as shown in FIG. 7 by a pulse signal with a duty factor of 1 to 11 at a peak current of 260 mA at a repetition rate of 500 pps for a time of 147 hours. Light intensity at 324.7 nm radiated from Cu for zero operating time is assumed to be 100. Shielding cylinder is 16 mm in length.

The result of the experiment indicates that the inner diameter of the cylindrical shield should be in the range of 8 mm to 16 mm if the length thereof is specified as 16 mm.

Smaller inner diameter than 8 mm may result in blocking of the light from the cathode due to deposition of the cathode material on the inner wall of the cylindrical shield.

Large inner diameter than 16 mm may result in passing of the cathode material through the cylindrical shield without efficient deposition of the cathode material on the inner wall.

The same result holds for the second embodiment of the present invention.

As described heretofore, the hollow cathode lamp in accordance with the present invention is characterized by the cylindrical shield, to effectively block the evaporated cathode material from the light emission window, arranged in a space between the cathode and light emission material, and the cylindrical shield greatly improves the life of the hollow cathode lamp as compared with the conventional disk-like shield.

What is claimed is:

1. In a hollow cathode lamp usable as a light source for atomic absorption and scintillation spectroscopies including a sealed envelope containing an inert gas and provided with a light emission window, a cathode disposed in said envelope opposite said window, and an anode disposed in said envelope coaxially with said cathode and between said cathode and said light emission window; the improvement wherein said anode consists of a metal cylinder having a uniform inner diameter D over its entire length L, said diameter D being greater than the diameter of said cathode, and wheren L is equal to or greater than D, whereby said metal cylinder forming said anode further acts to trap evaporated cathode material so as to block the diffusion of evaporated cathode material to said light emission window.

2. A hollow cathode lamp as defined in claim 1 wherein said cathode has an end surface facing said light emission window, and wherein said entire anode is axially displaced from said end surface of said cathode.

3. A hollow cathode lamp as defined in claim 2 further comprising a cylinder of insulating material enclosing said cathode except for said end surface of said cathode; and wherein said metal cylinder forming said anode has substantially the same diameter as said cylinder of insulating material.

4. A hollow cathode lamp as defined in claim 1 wherein said inner diameter D of said anode is equal to 13 mm.

5. A hollow cathode lamp as defined in claim 1 wherein said length L is equal to 16 mm and said inner diameter D of said anode is equal to or greater than 8 mm and less than 16 mm.

6. A hollow cathode lamp as defined in claim 5 wherein said inner diameter D is less than 13 mm.

7. In a hollow cathode lamp usable as a light source for atomic absorption and scintillation spectroscopies including a sealed envelope containing an inert gas and provided with a light emission window, a hollow cathode disposed in said envelope with its open end facing said window, an anode disposed in said envelope between said open end of said cathode and said light emission window, and a cylinder of insulating material surrounding said cathode and coaxial with same; the improvement wherein: means, surrounding the optical path between said open end of said cathode and said light emission window, for trapping evaporated cathode material to block the diffusion of the evaporated cathode material to said light emission window are provided, with said means comprising an extension of said cylinder of insulating material beyond said open end of said cathode in the direction of said light emission window such that the length of said extension is greater than the inner diameter of said cylinder; and said anode is a rod which extends into the interior of said extension of said cylinder of insulating material via an aperture in the side wall of said cylinder.

* * * * *